United States Patent
Horiuti et al.

(10) Patent No.: US 8,357,772 B2
(45) Date of Patent: Jan. 22, 2013

(54) TERMINALLY IODIZED POLYFLUOROALKANE AND METHOD FOR PRODUCING THE SAME

(75) Inventors: Masayosi Horiuti, Ibaraki (JP); Seiichiro Murata, Ibaraki (JP); Katsuyuki Sato, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 295 days.

(21) Appl. No.: 12/677,579

(22) PCT Filed: Aug. 29, 2008

(86) PCT No.: PCT/JP2008/065541
§ 371 (c)(1),
(2), (4) Date: Mar. 11, 2010

(87) PCT Pub. No.: WO2009/034859
PCT Pub. Date: Mar. 19, 2009

(65) Prior Publication Data
US 2010/0261869 A1    Oct. 14, 2010

(30) Foreign Application Priority Data
Sep. 12, 2007  (JP) .................. 2007-236315

(51) Int. Cl.
*C08G 61/04* (2006.01)
*C08G 61/00* (2006.01)

(52) U.S. Cl. ......... 528/397; 528/401; 528/392; 526/249

(58) Field of Classification Search ................ 526/249; 528/397, 401, 392
See application file for complete search history.

(56) References Cited

U.S. PATENT DOCUMENTS
4,810,765 A * 3/1989 Modena et al. ............... 526/249

FOREIGN PATENT DOCUMENTS

| | | |
|---|---|---|
| JP | 60104023 | 6/1985 |
| JP | 60106533 | 6/1985 |
| JP | 2004-269413 | 9/2004 |
| JP | 2005-179524 | 7/2005 |
| WO | WO20007/102371 A1 | 9/2007 |

OTHER PUBLICATIONS

Aigbirhio, Franklin et al., "*Labelling of the CFC-Alternative, 2H-heptafluoropropane (HFC 227ea), with Fluorine-18*", Journal of Fluorine Chemistry, 1995, vol. 75, pp. 67-73.

Balague, J. et al., "*Controlled Step-wise Telomerization of Vinylidene Fluoride, Hexafluoropropene and Trifluoroethylene with Iodofluorinated Transfer Agents*", Journal of Fluorine Chemistry, 2000, vol. 102, pp. 253-268.

Balague, J. et al. "*Synthesis of Fluorinated Telomers. Part 1. Elomerization of Vinylidene Fluoride with Perfluoroalkyl Iodides*", Journal of Fluorine Chemistry, 1995, vol. 70, pp. 215-223.

Dougherty, Thomas, "*Structure of Vinyl Fluoride-Trifluoromethyl Iodide Telomoers*", Journal of American Chemical Society, 1964, vol. 86, No. 3, p. 450-463.

International Search Report from corresponding PCT application No. PCT/JP2008/065541, dated Dec. 9, 2008, 4 pages.

English translation of International Preliminary Report on Patentability (Chapter I) and Written Opinion from corresponding PCT application No. PCT/JP2008/065541, dated Apr. 8, 2010, 6 pages.

* cited by examiner

*Primary Examiner* — Duc Troung
(74) *Attorney, Agent, or Firm* — Brinks Hofer Gilson & Lione

(57) ABSTRACT

Provided is a terminally iodized polyfluoroalkane represented by the general formula:

$$C_nF_{2n+1}(CHXCFY)_{s+p}(CF_2CF_2)_{t+r}I \qquad [I]$$

(in the formula, X and Y are each a hydrogen atom or a fluorine atom, wherein when Y is a fluorine atom, X is also a fluorine atom; n is an integer of 1 to 6; s+p is an integer of 1 to 5 and denotes the number of CHXCFY group; and t+r is 0 or an integer of 1 to 6 and denotes the number of tetrafluoroethylene skeleton). The terminally iodized polyfluoroalkane is produced by telomerizing a fluorine-containing olefin CHX=CFY and tetrafluoroethylene, successively, to $C_nF_{2n+1}I$ in the presence of a peroxide initiator.

5 Claims, No Drawings

TERMINALLY IODIZED POLYFLUOROALKANE AND METHOD FOR PRODUCING THE SAME

RELATED APPLICATION

This application is a 35 U.S.C. §371 national phase filing of International Patent Application No. PCT/JP2008/065541, filed Aug. 28, 2008, through which and to which priority is claimed under 35 U.S.C. §119 to Japanese Patent Application No. 2007-236315, filed Sep. 12, 2007.

TECHNICAL FIELD

The present invention relates to a terminally iodized polyfluoroalkane and a method for producing the same. More specifically, the present invention relates to a terminally iodized polyfluoroalkane in which a fluorine-containing olefin is telomerized and a method for producing the same.

BACKGROUND ART

It is known a method for telomerizing vinylidene fluoride using a perfluoroalkyl iodide as a starting raw material and a metal or metal complex as a catalyst. In addition, it is known a method for performing telomerization in the presence of a radical generator under a high temperature, a high pressure, or a high temperature and a high pressure condition. A reaction under a high temperature and/or a high pressure needs a large amount of energy. Furthermore, corrosion of facilities due to hydrofluoric acid or the like that is generated during the reaction becomes serious, and thereby the frequency of renewal of the facilities is increased. On the other hand, when a corrosion resistant material is used, since such a material is expensive, it cannot be avoided that the facilities are expensive.

[Patent Document 1] JP-A-60-106533
[Patent Document 2] JP-A-60-104023
[Non-Patent Document 1] J. Fluorine Chem., 70, 215 (1995)
[Non-Patent Document 2] J. Fluorine Chem., 102, 253 (2000)

It has been reported that compounds of which telomer-terminal perfluoroalkyl group having about 8 carbon atoms obtained in the above have high bioaccumulation potential and have an environmental problem. Therefore, it is concerned that the manufacturing and the use of these compounds will become difficult in the future. However, compounds including perfluoroalkyl groups having 6 or less carbon atoms are recognized to be low in bioaccumulation potential.

DISCLOSURE OF THE INVENTION

Problem to be Solved by the Invention

It is an object of the present invention to provide a terminally iodized polyfluoroalkane being a compound including a perfluoroalkyl group having 6 or less carbon atoms, known to be low in bioaccumulation potential, in which a fluorine-containing olefin is telomerized, and to provide a method for producing the same.

Means for Solving the Problem

According to the present invention, provided is a terminally iodized polyfluoroalkane represented by the general formula:

$$C_nF_{2n+1}(CHXCFY)_{s+p}(CF_2CF_2)_{t+r}I \quad [I]$$

(in the formula, X and Y are each a hydrogen atom or a fluorine atom, wherein when Y is a fluorine atom, X is also a fluorine atom; n is an integer of 1 to 6; s+p is an integer of 1 to 5 and denotes the number of CHXCFY group; and t+r is 0 or an integer of 1 to 6 and denotes the number of tetrafluoroethylene skeleton). Here, usually, the compound can be a mixture of those having various values of n, s+p, and t+r, regulating the compound [I].

The terminally iodized polyfluoroalkane is produced by reacting a terminally iodized polyfluoroalkane represented by the general formula:

$$C_nF_{2n+1}(CHXCFY)_{s+p}(CF_2CF_2)_tI \quad [II]$$

(in the formula, X and Y are each a hydrogen atom or a fluorine atom, wherein when Y is a fluorine atom, X is also a fluorine atom; n is an integer of 1 to 6; s+p is an integer of 1 to 5 and denotes the number of CHXCFY group; and t is an integer of 0 to 3 and denotes the number of tetrafluoroethylene skeleton in a raw material) with tetrafluoroethylene in the presence of a peroxide initiator, and is obtained as a terminally iodized polyfluoroalkane represented by the general formula:

$$C_nF_{2n+1}(CHXCFY)_{s+p}(CF_2CF_2)_{t+r}I \quad [I]$$

(in the formula, X, Y, n, s+p, and t are defined as the same as the above; and r is an integer of 1 to 5 and denotes the number of tetrafluoroethylene skeleton added by the reaction, wherein t+r is an integer of 1 to 6). As the compound [II], a mixture of compounds having various n values, s+p values, and t values can be used.

In addition, a terminally iodized polyfluoroalkane [IV], which is a compound [II] being t=0, is produced by telomerizing a fluorine-containing olefin represented by the general formula:

$$CHX{=}CFY$$

(in the formula, X and Y are each a hydrogen atom, wherein when Y is a fluorine atom, X is also a fluorine atom) to a perfluoroalkyl iodide represented by the general formula:

$$C_nF_{2n+1}I \quad [III]$$

(in the formula, n is an integer of 1 to 6) in the presence of a peroxide initiator. In this case, the resulting terminally iodized polyfluoroalkane:

$$C_nF_{2n+1}(CHXCFY)_sI$$

is further applied to a reaction with the above fluorine-containing olefin, and thereby the terminally iodized polyfluoroalkane:

$$C_nF_{2n+1}(CHXCFY)_{s+p}I \quad [IV]$$

Can be formed by a multistage reaction.

Effects of the Invention

The terminally iodized polyfluoroalkane according to the present invention is not only constituted of a perfluoroalkyl group having 6 or less carbon atoms, which is low in bioaccumulation potential, but also includes a CHXCFY group in the molecule. Therefore, a double bond is easily formed by the elimination of HF from the CHXCFY group, which allows easy decomposition by ozonolysis, resulting in low in disturbance of environment.

In addition, regarding the application of the compound, a terminal (meth)acrylic acid ester can be formed by substituting the terminal iodine group by a terminal hydroxyl group and further reacting the terminal hydroxyl group with (meth)acrylic acid. Since the ester can form, for example, a surfactant, a water- and oil-repellent, a surface-modifying agent and the like, the terminally iodized polyfluoroalkane can be effectively used as a raw material for synthesizing such derivative compounds.

BEST MODE FOR CARRYING OUT THE INVENTION

The terminally iodized polyfluoroalkane [II] serving as a raw material for synthesizing the terminally iodized polyfluoroalkane [I] is obtained by reacting a perfluoroalkyl iodide represented by the general formula:

$$C_nF_{2n+1}I \qquad [III]$$

n: an integer of 1 to 6,
with a fluorine-containing olefin in the presence of a peroxide initiator, and then by reacting the resulting terminally iodized polyfluoroalkane represented by the general formula:

$$C_nF_{2n+1}(CHXCFY)_{s+p}I \qquad [IV]$$

s+p: 1 to 5 and denotes the number of CHXCFY group, as a starting raw material, with tetrafluoroethylene in the presence of a peroxide initiator.

Examples of the perfluoroalkyl iodide [III] include the following compounds:
$CF_3I$,
$CF_3CF_2I$,
$CF_3(CF_2)_2I$,
$CF_3(CF_2)_3I$,
$CF_3(CF_2)_4I$, and
$CF_3(CF_2)_5I$.

Examples of the fluorine-containing olefin to be reacted with such a perfluoroalkyl iodide include compounds represented by the general formula:

$$CHX=CFY \qquad [V]$$

X and Y: each a hydrogen atom or a fluorine atom, wherein when Y is a fluorine atom, X is also a fluorine atom,
and specifically include vinyl fluoride, 1,2-difluoroethylene, and trifluoroethylene.

Examples of the peroxide initiator used in each of the telomerization reaction of the fluorine-containing olefin CHX=CFY and the subsequent telomerization reaction of the tetrafluoroethylene include di-tert-butyl peroxide, di(4-tert-butylcyclohexyl)peroxy dicarbonate, dicetylperoxy dicarbonate, di-n-propylperoxy dicarbonate, diisopropylperoxy dicarbonate, and di-sec-butylperoxy dicarbonate. These organic peroxide initiators are each used in an amount of about 0.05 to 0.5% by mol and preferably about 0.1 to 0.25% by mol based on the amount of the perfluoroalkyl iodide [III] or the terminally iodized compound [IV], from the viewpoints of progression and control of the reaction.

The telomerization products [IV] of a fluorine-containing olefin is a mixture of those having various s+p values, and a telomerization product of the fluorine-containing olefin having a specific s+p value can be isolated by distilling the mixture. Oligomers not having a predetermined s+p value can be, after isolation or directly as the mixture, subjected again to telomerization with a fluorine-containing olefin.

The fluorine-containing olefin telomerization product:

$$C_nF_{2n+1}(CHXCFY)_{s+p}I \qquad [IV]$$

gives a terminally iodized polyfluoroalkane:

$$C_nF_{2n+1}(CHXCFY)_{s+p}(CF_2CF_2)_tI \qquad [II]$$

t: 0 to 3 by a telomerization reaction with tetrafluoroethylene in the presence of a peroxide initiator. The product [II] is a mixture containing a compound of t=0.

The terminally iodized polyfluoroalkane [I] as a target product of the present invention is obtained by further telomerizing tetrafluoroethylene [TFE] to the terminally iodized polyfluoroalkane [II] serving as a synthesis raw material in the presence of a peroxide initiator. As the peroxide initiator used in the telomerization reaction of TFE, the above-mentioned organic peroxide initiators are used in similar amounts.

$$C_nF_{2n+1}(CHXCFY)_{s+p}(CF_2CF_2)_{t+r}I \qquad [I]$$

t+r: 1 to 6 (r: the number of TFE skeleton added).

The temperatures for telomerization of the fluorine-containing olefin CHX=CFY and the tetrafluoroethylene depend on the decomposition temperature of the initiator used, but a reaction at a temperature of 80° C. or less is possible even under a low-pressure condition by using a peroxide initiator that is decomposed at a low temperature, such as di(4-tert-butylcyclohexyl)peroxy dicarbonate. That the reaction can be performed at low temperature allows not only a reduction in energy consumption but also suppression of corrosion due to hydrofluoric acid or the like, resulting in facilities to reduce the frequency of renewal of the facilities. In addition, since further inexpensive materials can be used, in conjunction with the reduction in frequency of renewal, the investment cost for the facilities can be reduced.

The telomerization reaction of the fluorine-containing olefin CHX=CFY and the subsequent telomerization reaction of tetrafluoroethylene are performed as follows: a perfluoroalkyl iodide [III] or a terminally iodized polyfluoroalkane [IV] or [II] is put in an autoclave; the inner temperature of the autoclave is increased to about 10 to 60° C., for example, 50° C.; then a peroxide initiator dissolved in a perfluoroalkyl iodide [III] or a terminally iodized polyfluoroalkane [IV] or [II] is added thereto; and when the inner temperature is increased to, for example, 55° C., a desired amount of a fluorine-containing olefin CHX=CFY or tetrafluoroethylene is fractionally added while maintaining a pressure of about 0.1 to 10 MPa; and then aging is performed at a temperature range of, for example, about 55 to 80° C. for about 1 hour. The values p and r, namely, the number of the fluorine-containing olefin CHX=CFY and the number of the tetrafluoroethylene skeleton added by the reactions are affected by the addition amounts thereof. However, the resulting products are each a mixture of those having various s+p values or t+r values.

Examples of the terminally iodized polyfluoroalkane [I] as the final product include the following compounds:
$C_2F_5(CHFCF_2)(CF_2CF_2)I$,
$C_2F_5(CHFCF_2)(CF_2CF_2)_2I$,
$C_2F_5(CHFCF_2)_2(CF_2CF_2)I$,
$C_2F_5(CHFCF_2)_2(CF_2CF_2)_2I$,
$C_4F_9(CHFCF_2)(CF_2CF_2)I$,
$C_4F_9(CHFCF_2)(CF_2CF_2)_2I$,
$C_4F_9(CHFCF_2)_2(CF_2CF_2)I$,
$C_4F_9(CHFCF_2)_2(CF_2CF_2)_2I$,
$C_2F_5(CH_2CHF)(CF_2CF_2)I$,
$C_2F_5(CH_2CHF)(CF_2CF_2)_2I$,
$C_2F_5(CH_2CHF)_2(CF_2CF_2)I$,
$C_2F_5(CH_2CHF)_2(CF_2CF_2)_2I$,
$C_4F_9(CH_2CHF)(CF_2CF_2)I$,
$C_4F_9(CH_2CHF)_2(CF_2CF_2)I$,
$C_4F_9(CH_2CHF)_2(CF_2CF_2)_2I$,
$C_4F_9(CH_2CHF)_2(CF_2CF_2)_2I$,
$C_2F_5(CHFCHF)(CF_2CF_2)I$,
$C_2F_5(CHFCHF)(CF_2CF_2)_2I$,
$C_2F_5(CHFCHF)_2(CF_2CF_2)I$, $C_2F_5(CHFCHF)_2(CF_2CF_2)_2I$,
$C_4F_9(CHFCHF)(CF_2CF_2)I$,
$C_4F_9(CHFCHF)_2(CF_2CF_2)I$,
$C_4F_9(CHFCHF)(CF_2CF_2)_2I$, and
$C_4F_9(CHFCHF)_2(CF_2CF_2)_2I$.

The telomerization product [I] of tetrafluoroethylene is a mixture of terminally iodized polyfluoroalkanes having various t+r values, and a terminally iodized polyfluoroalkane having a specific t+r value can be isolated by distilling the mixture. Terminally iodized polyfluoroalkanes not having a predetermined t+r value can be, after isolation or directly as the mixture, subjected again to telomerization with tetrafluoroethylene.

The present invention will be described with reference to Examples below.

EXAMPLE 1

In a 1200-mL autoclave, 500 g of perfluorobutyl iodide $C_4F_9I$ (purity: 82.9%) was put. When the inner temperature of the autoclave was increased to 50° C., 0.75 g (0.13% by mol) of a di(4-tert-butylcyclohexyl)peroxy dicarbonate initiator (Percadox 16: product of Kayaku Akzo Co., Ltd.) dissolved in 50 g of $C_4F_9I$ was added to the autoclave. When the inner temperature was increased to 55° C., 274 g of trifluoroethylene was fractionally added thereto while maintaining a pressure of 0.5 to 0.7 MPa. Then the reaction was terminated by aging at 55 to 70° C. for 1 hour. After the completion of the reaction and then cooling, 625 g of a product was collected.

The resulting product was isolated by distillation under conditions of a column top temperature of 62° C. and a pressure of 7.5 kPa to obtain 232 g of $CF_3(CF_2)_3(CHFCF_2)I$ (purity: 99.5%). The resulting purified reaction product was confirmed by the results of $^1$H-NMR and $^{19}$F-NMR to be the compound represented by the following formula and was used as a reaction raw material in Examples 2 and 3.

$CF_3CF_2CF_2CF_2(CHFCF_2)I$
$^1$H-NMR ($CDCl_3$, TMS): δ3.61 ($CHFCF_2$)
$^{19}$F-NMR ($CDCl_3$, $C_6F_6$): ppm −81.9 ($CF_3CF_2$)
−126.9 ($CF_3CF_2$)
−124.4 ($CF_2CF_2CF_2$)
−117.7 ($CF_2CF_2CF_2$)
−113.8 ($CHFCF_2$)
−49.3 ($CHFCF_2$)

EXAMPLE 2

In a 1200-mL autoclave, 800 g of $CF_3(CF_2)_3(CHFCF_2)I$ (purity: 99.5%) was put. When the inner temperature of the autoclave was increased to 50° C., 1.35 g (0.15% by mol) of a peroxide initiator (Percadox 16) dissolved in 100 g of $CF_3(CF_3)_3(CHFCF_2)I$ was added to the autoclave. When the inner temperature was increased to 55° C., 150 g of tetrafluoroethylene was fractionally added thereto while maintaining a pressure of 0.2 to 0.3 MPa. Then the reaction was terminated by aging at 55 to 75° C. for 1 hour. After the completion of the reaction and then cooling, 1010 g of a product was collected.

The resulting product was isolated by distillation under conditions of a column top temperature of 75° C. and a pressure of 2.5 kPa to obtain 314 g of $CF_3(CF_2)_3(CHFCF_2)(CF_2CF_2)I$ (purity: 99.4%). The resulting purified reaction product was confirmed by the results of $^1$H-NMR and $^{19}$F-NMR to be the compound represented by the following formula and was used as a reaction raw material in Example 3.

$CF_3CF_2CF_2CF_2(CHFCF_2)CF_2CF_2I$
$^1$H-NMR ($CDCl_3$, TMS): δ3.09 ($CHFCF_2$)
$^{19}$F-NMR ($CDCl_3$, $C_6F_6$): ppm −82.0 ($CF_3CF_2$)
−127.0 ($CF_3CF_2$)
−124.2 ($CF_2CF_2CF_2$)
−117.4 ($CF_2CF_2CF_2$)
−121.8 ($CHFCF_2$)
−112.5 ($CHFCF_2$)
−116.5 ($CF_2CF_2I$)
−59.9 ($CF_2CF_2I$)

EXAMPLE 3

In a 1200-mL autoclave, 800 g of a mixture (a weight ratio of 34.3:65.0) of
$CF_3(CF_2)_3(CHFCF_2)I$ (purity: 99.5%) and
$CF_3(CF_2)_3(CHFCF_2)(CF_2CF_2)I$ (purity: 99.4%)
was put. When the inner temperature of the autoclave was increased to 50° C., 1.68 g (0.18% by mol) of a peroxide initiator (Percadox 16) dissolved in 300 g of the mixture having such a mixture composition was added to the autoclave. When the inner temperature was increased to 55° C., 150 g of tetrafluoroethylene was fractionally added thereto while maintaining a pressure of 0.2 to 0.3 MPa. Then the reaction was terminated by aging at 55 to 75° C. for 1 hour. After the completion of the reaction and then cooling, 1208 g of a mixture product was collected.

The resulting product was isolated by distillation to obtain 149 g of $CF_3(CF_2)_3(CHFCF_2)I$ (purity: 99.8%), 515 g of $CF_3(CF_2)_3(CHFCF_2)(CF_2CF_2)I$ (purity: 99.6%), and 263 g of $CF_3(CF_2)_3(CHFCF_2)(CF_2CF_2)_2I$ (purity: 99.3%). The isolation by distillation was performed under the same distillation conditions as above for the $CF_3(CF_2)_3(CHFCF_2)I$ and the $CF_3(CF_2)_3(CHFCF_2)(CF_2CF_2)I$, and under conditions of a column top temperature of 93° C. and a pressure of 0.8 kPa for the $CF_3(CF_2)_3(CHFCF_2)(CF_2CF_2)_2I$. The resulting purified reaction product, $CF_3(CF_2)_3(CHFCF_2)(CF_2CF_2)_2I$, was confirmed by the results of $^1$H-NMR and $^{19}$F-NMR to be the compound represented by the following formula.

$CF_3CF_2CF_2CF_2(CHFCF_2)CF_2CF_2CF_2CF_2I$
$^1$H-NMR ($CDCl_3$, TMS): δ3.11 ($CHFCF_2$)
$^{19}$F-NMR ($CDCl_3$, $C_6F_6$): ppm −82.1 ($CF_3CF_2$)
−127.1 ($CF_3CF_2$)
−124.1 ($CF_3CF_2CF_2$)
−117.7 ($CF_3CF_2CF_2$)
−122.8 ($CHFCF_2$)
−117.9 ($CHFCF_2$)
−122.3 ($CF_2CF_2CF_2CF_2I$)
−124.2 ($CF_2CF_2CF_2CF_2I$)
−115.3 ($CF_2CF_2CF_2CF_2I$)
−60.8 ($CF_2CF_2CF_2CF_2I$)

The analysis results of gas chromatography (GC) of the products obtained in Examples above are shown as GC% values (calculated from the peak areas) of compounds having various n values, s(+p) values, and t(+r) values shown in the following Table 1 and represented by the formula:

$C_nF_{2n+1}(CHFCF_2)_{s(+p)}(CF_2CF_2)_{t(+r)}$.

TABLE 1

|   |   |   | Example 1 | | Example 2 | | Example 3 | |
|---|---|---|---|---|---|---|---|---|
| N | s (+p) | t (+r) | Raw Material | Product | Raw Material | Product | Raw Material | Product |
| 4 | 0 | 0 | 82.9 | 5.2 | | | | |
| 4 | 1 | 0 | | 57.2 | 99.5 | 41.2 | 34.3 | 13.9 |
| 4 | 2 | 0 | | 23.5 | | | | |
| 4 | 3 | 0 | | 4.0 | | | | |
| 4 | 4 | 0 | | 1.1 | | | | |

TABLE 1-continued

|   |       |       | Example 1 | | Example 2 | | Example 3 | |
|---|-------|-------|-----------|--|-----------|--|-----------|--|
| N | s (+p) | t (+r) | Raw Material | Product | Raw Material | Product | Raw Material | Product |
| 4 | 5 | 0 |  | 0.1 |  |  |  |  |
| 4 | 1 | 1 |  |  | 35.0 |  | 65.0 | 44.1 |
| 4 | 1 | 2 |  |  | 16.5 |  |  | 24.9 |
| 4 | 1 | 3 |  |  | 5.5 |  |  | 9.6 |
| 4 | 1 | 4 |  |  | 0.9 |  |  | 3.3 |
| 4 | 1 | 5 |  |  | 0.1 |  |  | 1.0 |
| 4 | 1 | 6 |  |  |  |  |  | 0.1 |
| $C_6F_{13}H$ |  |  | 16.7 | 8.5 |  |  |  |  |

Notes:
$C_6F_{13}H(CF_3CF_2CF_2CF_2CF_2H)$ is an impurity contained in a raw material $C_4F_9I$ and is a substance having a boiling point that is close to that of $C_4F_9I$ and therefore is difficult to be removed, but does not participate the reaction and is therefore used in the subsequent reaction without being removed.

EXAMPLE 4

In a 1200-mL autoclave, 500 g of perfluorobutyl iodide $C_4F_9I$ (purity: 82.9%) was put. When the inner temperature of the autoclave was increased to 50° C., 0.75 g (0.13% by mol) of a peroxide initiator (Percadox 16) dissolved in 50 g of $C_4F_9I$ was added to the autoclave. When the inner temperature was increased to 55° C., 155 g of vinyl fluoride was fractionally added thereto while maintaining a pressure of 0.5 to 0.7 MPa. Then the reaction was terminated by aging at 55 to 70° C. for 1 hour. After the completion of the reaction and then cooling, 529 g of a product was collected.

The resulting product was isolated by distillation under conditions of a column top temperature of 53° C. and a pressure of 7.5 kPa to obtain 276 g of $CF_3(CF_2)_3(CH_2CHF)I$ (purity: 99.5%). The resulting purified reaction product was confirmed by the results of $^1H$-NMR and $^{19}F$-NMR to be the compound represented by the following formula and was used as a reaction raw material in Examples 5 and 6.

$CF_3CF_2CF_2CF_2(CH_2CHF)I$
$^1H$-NMR (CDCl$_3$, TMS): δ2.82 (CH$_2$CHF)
3.41 (CH$_2$CHF)
$^{19}F$-NMR (CDCl$_3$, C$_6$F$_6$): ppm −81.9 (CF$_3$CF$_2$)
−126.7 (CF$_3$CF$_2$)
−125.7 (CF$_2$CF$_2$CF$_2$)
−111.8 (CF$_2$CF$_2$CF$_2$)
−27.7 (CH$_2$CHF)

EXAMPLE 5

In a 1200-mL autoclave, 800 g of $CF_3(CF_2)_3(CH_2CHF)I$ (purity: 99.5%) was put. When the inner temperature of the autoclave was increased to 50° C., 1.35 g (0.15% by mol) of a peroxide initiator (Percadox 16) dissolved in 100 g of $CF_3(CF_2)_3(CH_2CHF)I$ was added to the autoclave. When the inner temperature was increased to 55° C., 140 g of tetrafluoroethylene was fractionally added thereto while maintaining a pressure of 0.2 to 0.3 MPa. Then the reaction was terminated by aging at 55 to 75° C. for 1 hour. After the completion of the reaction and then cooling, 974 g of a product was collected.

The resulting product was isolated by distillation under conditions of a column top temperature of 67° C. and a pressure of 2.7 kPa to obtain 328 g of $CF_3(CF_2)_3(CH_2CHF)(CF_2CF_2)I$ (purity: 99.4%). The resulting purified reaction product was confirmed by the results of $^1H$-NMR and $^{19}F$-NMR to be the compound represented by the following formula and was used as a reaction raw material in Example 6.

$CF_3CF_2CF_2CF_2(CH_2CHF)CF_2CF_2I$
$^1H$-NMR (CDCl$_3$, TMS): δ2.28 (CH$_2$CHF)
2.89 (CH$_2$CHF)
$^{19}F$-NMR (CDCl$_3$, C$_6$F$_6$): ppm −82.0 (CF$_3$CF$_2$)
−126.8 (CF$_3$CF$_2$)
−125.5 (CF$_2$CF$_2$CF$_2$)
−111.5 (CF$_2$CF$_2$CF$_2$)
−110.9 (CH$_2$CHF)
−117.2 (CF$_2$CF$_2$I)
−58.4 (CF$_2$CF$_2$I)

EXAMPLE 6

In a 1200-mL autoclave, 800 g of a mixture (a weight ratio of 35.1:64.3) of
$CF_3(CF_2)_3(CH_2CHF)I$ (purity: 99.5%) and
$CF_3(CF_2)_3(CH_2CHF)(CF_2CF_2)I$ (purity: 99.4%)
was put. When the inner temperature of the autoclave was increased to 50° C., 1.68 g (0.18% by mol) of a peroxide initiator (Percadox 16) dissolved in 300 g of the mixture having such a mixture composition was added to the autoclave. When the inner temperature was increased to 55° C., 140 g of tetrafluoroethylene was fractionally added thereto while maintaining a pressure of 0.2 to 0.3 MPa. Then the reaction was terminated by aging at 55 to 75° C. for 1 hour. After the completion of the reaction and then cooling, 1177 g of a mixture product was collected.

The resulting product was isolated by distillation to obtain 139 g of $CF_3(CF_2)_3(CH_2CHF)I$ (purity: 99.7%), 541 g of $CF_3(CF_2)_3(CH_2CHF)(CF_2CF_2)I$ (purity: 99.6%), and 240 g of $CF_3(CF_2)_3(CH_2CHF)(CF_2CF_2)_2I$ (purity: 99.4%). The isolation by distillation was performed under the same distillation conditions as above for the $CF_3(CF_2)_3(CH_2CHF)I$ and the $CF_3(CF_2)_3(CH_2CHF)(CF_2CF_2)I$, and under conditions of a column top temperature of 89° C. and a pressure of 1.0 kPa for the $CF_3(CF_2)_3(CH_2CHF)(CF_2CF_2)_2I$. The resulting purified reaction product, $CF_3(CF_2)_3(CH_2CHF)(CF_2CF_2)_2I$, was confirmed by the results of $^1H$-NMR and $^{19}F$-NMR to be the compound represented by the following formula.

$CF_3CF_2CF_2CF_2(CH_2CHF)CF_2CF_2CF_2CF_2I$
$^1H$-NMR (CDCl$_3$, TMS): δ2.39 (CH$_2$CHF)
2.99 (CH$_2$CHF)
$^{19}F$-NMR (CDCl$_3$, C$_6$F$_6$): ppm −82.1 (CF$_2$CF$_2$)
−126.9 (CF$_3$CF$_2$)
−125.4 (CF$_2$CF$_2$CF$_2$)
−111.8 (CF$_2$CF$_2$CF$_2$)
−112.4 (CH$_2$CHF)
−123.2 (CF$_2$CF$_2$CF$_2$CF$_2$I)
−124.9 (CF$_2$CF$_2$CF$_2$CF$_2$I)
−116.0 (CF$_2$CF$_2$CF$_2$CF$_2$I)
−59.3 (CF$_2$CF$_2$CF$_2$CF$_2$I)

The analysis results of gas chromatography (GC) of the products obtained in Examples above are shown as GC% values (calculated from the peak areas) of compounds having various n values, s(+p) values, and t(+r) values shown in the following Table 1 and represented by the formula:

$C_nF_{2n+1}(CH_2CHF)_{s(+p)}(CF_2CF_2)_{t(+r)}I$.

TABLE 1

|   |       |       | Example 4 | | Example 5 | | Example 6 | |
|---|-------|-------|-----------|--|-----------|--|-----------|--|
| n | s (+p) | t (+r) | Raw Material | Product | Raw Material | Product | Raw Material | Product |
| 4 | 0 | 0 | 82.9 | 5.2 |  |  |  |  |
| 4 | 1 | 0 |  | 65.2 | 99.5 | 41.4 | 35.1 | 14.1 |
| 4 | 2 | 0 |  | 17.9 |  |  |  |  |
| 4 | 3 | 0 |  | 2.5 |  |  |  |  |

TABLE 1-continued

|  |  |  | Example 4 | | Example 5 | | Example 6 | |
| --- | --- | --- | --- | --- | --- | --- | --- | --- |
| n | s (+p) | t (+r) | Raw Material | Product | Raw Material | Product | Raw Material | Product |
| 4 | 4 | 0 |  | 0.2 |  |  |  |  |
| 4 | 1 | 1 |  |  |  | 38.2 | 64.3 | 47.9 |
| 4 | 1 | 2 |  |  |  | 13.2 |  | 23.1 |
| 4 | 1 | 3 |  |  |  | 3.1 |  | 8.2 |
| 4 | 1 | 4 |  |  |  | 0.7 |  | 2.8 |
| 4 | 1 | 5 |  |  |  | 0.1 |  | 0.9 |
| 4 | 1 | 6 |  |  |  |  |  | 0.1 |
| $C_6F_{13}H$ |  |  | 16.7 | 7.5 |  |  |  |  |

The invention claimed is:

1. A terminally iodized polyfluoroalkane represented by the general formula:

$$C_nF_{2n+1}(CHXCFY)_{s+p}(CF_2CF_2)_{t+r}I \quad [I]$$

(in the formula, X and Y are each a hydrogen atom or a fluorine atom, wherein when Y is a fluorine atom, X is also a fluorine atom; n is an integer of 1 to 6; s+p is an integer of 1 to 5 and denotes the number of CHXHFY groups; and t+r is an integer of 1 to 6 and denotes the number of tetrafluoroethylene skeleton).

2. The terminally iodized polyfluoroalkane according to claim 1, being a mixture of those having various n values, s+p values, and t+r values.

3. A method of producing a terminally iodized polyfluoroalkane represented by the general formula:

$$C_nF_{2n+1}(CHXCFY)_{s+p}(CF_2CF_2)_{t+r}I \quad [I]$$

(in the formula, X and Y are each a hydrogen atom or a fluorine atom, wherein when Y is a fluorine atom, X is also a fluorine atom; n is an integer of 1 to 6; s+p is an integer of 1 to 5 and denotes the number of CHXHFY groups; and t is an integers of 0 to 3 and denotes the number of tetrafluoroethylene skeleton in a raw material; and r is an integer of 1 to 5 and denotes the number of tetrafluoroethylene skeleton added by a reaction, wherein t+r is an integer of 1 to 6), the method comprising:

reacting a terminally iodized polyfluoroalkane represented by the general formula:

$$C_nF_{2n+1}(CHXCFY)_{s+p}(CF_2CF_2)_tI \quad [II]$$

(in the formula, X, Y, n, s+p, and t are defined as the same above) with tetrafluoroethylene in the presence of a peroxide initiator.

4. The method for producing a terminally iodized polyfluoroalkane according to claim 3, wherein the compound [II] is a mixture of those having various n values, s+p values, and t values.

5. The method for producing a terminally iodized polyfluoroalkane according to claim 3, wherein the reaction is conducted at a temperature of 80° C. or less.

* * * * *